United States Patent [19]

Roser et al.

[11] Patent Number: 5,958,455
[45] Date of Patent: Sep. 28, 1999

[54] ORAL SOLID DOSAGE FORMS, METHODS OF MAKING SAME AND COMPOSITIONS THEREOF

[75] Inventors: Bruce J. Roser, Road; Julian Blair, St. Ives; Camilo Colaco, Trumpington; Ross Henry Morris Hatley, Willingham, all of United Kingdom

[73] Assignee: Quadrant Holdings Cambridge Ltd, Trumpington, United Kingdom

[21] Appl. No.: 08/599,273

[22] Filed: Feb. 9, 1996

[51] Int. Cl.⁶ .................................................. A61K 9/14
[52] U.S. Cl. ............................................ 424/489; 424/464
[58] Field of Search .......................... 514/777; 424/400, 424/489, 458, 464, 470

[56] References Cited

U.S. PATENT DOCUMENTS

| | | |
|---|---|---|
| 3,557,717 | 1/1971 | Chivers . |
| 3,619,294 | 11/1971 | Black et al. . |
| 3,632,357 | 1/1972 | Childs . |
| 3,655,442 | 4/1972 | Schwer et al. . |
| 3,721,725 | 3/1973 | Briggs et al. . |
| 3,932,943 | 1/1976 | Briggs et al. . |
| 4,127,502 | 11/1978 | Li Mutti et al. . |
| 4,158,544 | 6/1979 | Louderback . |
| 4,327,076 | 4/1982 | Puglia et al. . |
| 4,327,077 | 4/1982 | Puglia et al. . |
| 4,588,744 | 5/1986 | McHugh . |
| 4,678,812 | 7/1987 | Bollin et al. ............................ 514/777 |
| 4,701,417 | 10/1987 | Portenhauser et al. . |
| 4,762,857 | 8/1988 | Bollin, Jr. et al. . |
| 4,865,871 | 9/1989 | Livesey et al. . |
| 4,879,280 | 11/1989 | Seyffart et al. . |
| 4,883,762 | 11/1989 | Hoskins . |
| 4,891,319 | 1/1990 | Roser .................................... 435/188 |
| 5,026,566 | 6/1991 | Roser . |
| 5,149,653 | 9/1992 | Roser . |
| 5,290,765 | 3/1994 | Wettlaufer et al. . |
| 5,306,506 | 4/1994 | Zema et al. . |
| 5,348,852 | 9/1994 | Bonderman . |
| 5,422,384 | 6/1995 | Samuels et al. . |
| 5,425,951 | 6/1995 | Goodrich, Jr. et al. . |
| 5,512,547 | 4/1996 | Johnson et al. . |
| 5,589,167 | 12/1996 | Cleland et al. . |

FOREIGN PATENT DOCUMENTS

| | | |
|---|---|---|
| 415 567 A2 | 3/1991 | European Pat. Off. . |
| 600 730 A1 | 6/1994 | European Pat. Off. . |
| 606 753 A2 | 7/1994 | European Pat. Off. . |
| 619 951 A2 | 10/1994 | European Pat. Off. . |
| 628 630 A2 | 12/1994 | European Pat. Off. . |
| 636 693 A2 | 2/1995 | European Pat. Off. . |
| 0714905 | 6/1996 | European Pat. Off. . |
| 58-216695 | 12/1983 | Japan . |
| 6-70718 | 3/1994 | Japan . |
| 9977 | of 1844 | United Kingdom . |
| 1381588 | 1/1975 | United Kingdom . |
| 2 206 273 | 1/1989 | United Kingdom . |
| 87/00196 | 1/1987 | WIPO . |
| 89/06542 | 7/1989 | WIPO . |
| 92/02133 | 2/1992 | WIPO . |
| 93/02834 | 2/1993 | WIPO . |
| 93/10758 | 6/1993 | WIPO . |
| 93/11220 | 6/1993 | WIPO . |
| 94/15636 | 7/1994 | WIPO . |
| 95/06126 | 3/1995 | WIPO . |
| 95/33488 | 12/1995 | WIPO . |

OTHER PUBLICATIONS

Dialog® English Abstract of JP 58–216695 (Dec. 16, 1983).
Dialog® WPI File 351 Abstract of PCT WO 87/05300 (Sep. 11, 1987).

(List continued on next page.)

Primary Examiner—Thurman K. Page
Assistant Examiner—William E. Benston, Jr.
Attorney, Agent, or Firm—Susan K. Lehnhardt

[57] ABSTRACT

Methods of making tablets of a variety of physical forms are described. The tablets can be made into a wide variety of formulations. The invention further provides methods of making crystalline and amorphous anhydrous trehalose for use in formulating tablets suitable for use in dispensing pharmaceutical agents.

31 Claims, 5 Drawing Sheets

OTHER PUBLICATIONS

Sakurai, Y (ed.), "Food General Dictionary" Sixth Edition (The English translation is 10 pages total.).

Kanna et al., "Denaturation of Fish Muscle Protein by Dehydration–V." *Bull. Tokai Reg. Fish. Res. Lab.* (1974) 77:1–14.

Reasons for Opposition, (1995), 5 pages total.

Supplement of Reasons for Opposition (Dec. 31, 1995), 23 pages total.

Grounds for Rejection, (1995), 6 pages total.

Handbook of Natural Materials for Food Processing, Ninth Edition (Translation to be disclosed at a later date).

Chemical Dictionary, $7^{th}$ Edition (Translation to be disclosed at a later date).

*Stability and characterization of protein and peptide drugs*, Wang et al. (eds.), 1993, table of contents enclosed herewith.

Pogany et al., "A new approach to the theory of tabletting" *Acta Pharm. Hung.* (1988) 58:49–55.

Doelker, "Recent advances in tableting science" *Boll. Chim. Farm.* (1988) 127:37–49.

Hiestand et al., "Physical processes of tableting" *J. Pharm. Sci.* (1977) 66:510–519.

Cooper et al., "Tableting research and technology" *J. Pharm. Sci.* (1972) 61:1511–1555.

*Remington: The Science and Practice of Pharmacy*, Nineteenth Edition, Gennaro Ed. (1995) Mack Publishing Company, Pennsylvania vol. II, pp. 1615–1649.

Niwa et al., "Preparation of agglomerated crystals for direct tabletting and microencapsulation by the spherical crystallization technique with a continuous system" *Pharm. Res.* (1994) 11:478–484.

Franz et al., "Cost evaluation of alternative pharmaceutical tableting processes by simulation" *J. Pharm. Sci.* (1980) 69:621–628.

Lipps et al., "Characterization of wet granulation process parameters using response surface methodology. 1. Top–spray fluidized bed" *J. Pharm. Sci.* (1994) 83:937–947.

Drissi–Alami et al., "The effects of the tabletting machine speed on physical characteristics of pharmaceutical powders" *J. Pharm. Belg.* (1993) 48:43–52.

Ishino et al., "Influence of tabletting speed on compactibility and compressibility of two direct compressible powders under high speed compression" *Chem. Pharm. Bull.* (1990) 38:1987–1992.

Sendall et al., "A study of powder adhesion to metal surfaces during compression of effervescent pharmaceutical tablets" *J. Pharm. Pharmacol.* (1986) 38:489–493.

Jetzer, "Measurement of hardness and strength of tablets and their relation to compaction performance of powders" *J. Pharm. Pharmacol.* (1986) 38:254–258.

Reading et al., "The effects of binder film characteristics on granule and tablet properties" *J. Pharm. Pharmacol.* (1984) 36:421–426.

Paronen et al., "Compressional characteristics of four starches" *J. Pharm. Pharmacol.* (1983) 35:627–635.

Nakagawa, "Effects of tableting procedures on the preferred orientation of crystalline particles" *Chem. Pharm. Bull.* (1982) 30:1401–1407.

Elsabbagh et al., "Physical properties and dissolution profiles of acetaminophen and acetylsalicyclic acid tables made from sucrosebased vehicles" *Pharmazie* (1981) 36:488–492.

Naito et al., "Prediction of tableting problems such as capping and sticking: Theoretical calculations" *J. Pharm. Sci.* (1977) 66:254–259.

Healey et al., "The mechanical properties of some binders used in tableting" *J. Pharm. Pharmac.* (1974) 26 Suppl:41P–46P.

York et al., "The effect of temperature on the mechanical properties of some pharmaceutical powders in relation to tableting" *J. Pharm. Pharmac.* (1972) 24 Suppl:47P–56P.

Sebhatu et al., "Effect of moisture sorption on tabletting characteristics of spray dried (15% amorphous) lactose" *Pharm. Res.* (1994) 11:1233–1238.

Vromans et al., "Studies on tabletting properties of lactose. Part I. The effect of initial particle size on binding properties and dehydration characteristics of lactose" *Acta Pharm. Suec.* (1985) 22:163–172.

Vromans et al., "Studies on tabletting properties of lactose. Part 2. Consolidation and compaction of different types of crystalline lactose" *Pharm. Weekbl [Sci]* (1985) 7:186–193.

De Boer et al., "Studies on tabletting properties of lactose. Part III. The consolidation behaviour of sieve fractions of crystalline α–lactose monohydrate" *Pharm. Weekbl [Sci]* (1986) 8:145–150.

Van Kamp et al., "Studies on tableting properties of lactose. V. Effects of both lubrication and addition of disintegrants on properties of tablets prepared from different types of crystalline lactose" *Acta Pharm. Suec.* (1986) 23:217–230.

Vromans et al., "Studies on tabletting properties of lactose. VI. Consolidation and compaction of spray dried amorphous lactose" *Acta Pharm. Suec.* (1986) 23:231–240.

Georgakopoulos et al., "The effects of using different grades of PVP and gelatin as binders in the fluidized bed granulation and tabletting of lactose" *Pharmazie* (1983) 38:240–243.

York et al., "Science Papers. The tensile strength and compression behaviour of lactose, four fatty acids, and their mixtures in relation to tableting" *J. Pharm. Pharmac.* (1973) 25:Suppl:1P–11P.

Blakeley et al. "Dry instant blood typing plate for bedside use" *Lancet* (1990)336:854–855.

Roser, "Trehalose, a new approach to premium dried foods" *Trends in Food Sci. and Tech.*, (Jul. 1991) 166–169.

Colaco et al. "Trehalose stabilisation of biological molecules" *Biotechnol. Internat.* (1992) 345–350.

Roser, "Trehalose drying: A novel replacement for freeze–drying" *BioPharm* (1991) 4:47–53.

Colaco et al., "Extraordinary stability of enzymes dried in trehalose: Simplified molecular biology" *Bio/Tech.* (1992) 10:1007–1011.

Roser et al., "A sweeter way to fresher food" *New Scientist*, (May 1993) pp. 25–28.

Madzarovova–Nohejlova, "Trehalase deficiency in a family" *Gastroenterol.* (1973) 65:130–133.

Ravich et al., "Carbohydrate absorption and malabsorption" *Clin. Gast.* (1983) 12:335–356.

Sacktor, "Trehalose and the transport of glucose in the mammalian kidney and intestine" *Proc. Natl. Acad. Sci. USA* (1968) 60:1007–1014.

Belfiore et al., "Serum enzymes in diabetes mellitus" *Clin. Chem.* (1973) 19:447–452.

Eze, "Plasma trehalase activity and diabetes mellitus" *Biochem. Genet.* (1989) 27:487–495.

Yoshida et al. "Serum trehalase activity in patients with rheumatoid arthritis" *Clin. Chim. Acta* (1993) 215:123–124.

Kramers et al., "Cell membrane enzymes: L–γ–glutamyl transpeptidase, leucine aminopeptidase, maltase and trehalase in normal and leukaemic lymphocytes" *Brit. J. Haematol.* (1978) 38:453–461.

Bergoz et al., "Significance of duodenal disaccharidases. A comparative study of duodenal and jejunal values" *Digestion* (1981) 22:108–112.

Riby et al., Rat intestinal brush border membrane trehalase: Some properties of the purified enzyme *Comp. Biochem. Physiol.* (1985) 82B:821–827.

Chen et al., "Rat intestinal trehalase" *Biochem. J.* (1987) 247:715–724.

Maestracci, "Enzymic solubilization of the human intestinal brush border membrane enzymes" *Biochim. et Biophys. Acta* (1976) 433:469–481.

Galand, "Brush border membrane sucrase–isomaltase, maltase–glucoamylase and trehalase in mammals" *Comp. Biochem. Physiol* (1989) 94B:1–11.

ORAL SOLID DOSAGE FORMS, METHODS OF MAKING SAME AND COMPOSITIONS THEREOF

TECHNICAL FIELD

This invention relates to the use of trehalose dihydrate, amorphous trehalose and anhydrous trehalose in making tablets. Compositions in tablet form are also encompassed by the invention. The invention also encompasses methods of making various forms of anhydrous trehalose including amorphous, crystalline and mixtures thereof.

BACKGROUND

Drugs and other active agents are most frequently administered orally by means of solid dosage forms such as tablets and capsules. Large scale production methods used for their preparation usually require that they contain other materials in addition to the active ingredients. Additives may also be included in the formulations to facilitate handling, enhance the physical appearance, improve stability and aid in delivery of the drug to the bloodstream after administration.

Tablets are defined as solid pharmaceutical dosage forms containing drug substances with or without suitable diluents. Typically, each tablet contains a single dose of an effective amount of the pharmaceutical agent. Tablets are prepared by compression, extrusion or molding methods. Tablets are popular as a dosage form because of the advantages afforded both to the manufacturer (e.g., simplicity and economy of preparation, stability and convenience in packaging, shipping and dispensing) and the patient (e.g., accuracy of dosage, compactness, portability, blandness of taste and ease of administration). Tablets are the most common form of solid dose drug delivery. For review see, Pogany et al. (1988) Acta Pharm. Hung. 58:49–55; Doelker et al. (1988) Boll. Chim. Farm. 127:37–49; Hiestand et al. (1977) J. Pharm. Sci. 66:510–519; and Cooper et al. (1972) J. Pharm. Sci. 61:1511–1555.

Compressed tablets are usually prepared by large-scale production methods, while molded tablets generally involve small-scale operations. Compressed tablets usually contain no special coating and are made from a small number of powdered, crystalline or granular materials or "diluents," alone or in combination with disintegrants, controlled-release polymers, lubricants, diluents and, in many cases, colorants.

Compressed tablets may be coated with a variety of substances which may alter their physical characteristics. Sugar coated tablets contain a sugar coating which may be colored. Such coatings are beneficial in masking drugs possessing objectionable tastes or odors and in protecting materials sensitive to humidity, light or oxidation. Film-coated tablets are covered with a thin layer or film of water soluble or insoluble material. A number of polymeric substances with film forming properties can be used. Film coating imparts the same general characteristics as sugar coating with a much shorter period required for coating. Enteric coated tablets are coated with substances that resist dissolution in gastric fluid but disintegrate in the intestine. Enteric coatings are useful for tablets containing drugs that are inactivated or destroyed in the stomach, for those which irritate the mucosa or as a means of delayed release of the medication. Multiple compressed tablets are those made by more than one compression cycle. These include, layered tablets and press-coated tablets. Compressed tablets can be formulated into controlled-release tablets which release drug over a prolonged period of time to provide pulsatile or sustained release.

Compressed tablets can also be formed into tablets for purposes other than oral delivery. These include, but are not limited to, disintegration into solution, effervescent tablets, compressed suppositories or inserts, and buccal and sublingual tablets. Compressed tablets for preparing solutions include, for instance, Halzone Tablets for Solution and Potassium Permanganate Tablets for Solution. Effervescent tablets contain sodium bicarbonate and an organic acid such as tartaric or citric in addition to the drug. In the presence of water, these additives react to liberate carbon dioxide which acts as a disintegrator and provides effervescence. Sufficient acid is added to produce a neutral or slightly acidic reaction when disintegration in water is rapid and complete. Occasionally, vaginal suppositories, such as Metronidazole Tablets, are prepared by compression. Tablets for this use usually contain lactose as the diluent. Buccal and sublingual tablets are small, flat, oval tablets administered by insertion under the tongue or into the space between the cheek and gum where they dissolve slowly or erode; therefore, they are formulated and compressed with sufficient pressure to give a hard tablet. Progesterone or testosterone tablets may be administered in this manner.

There are a variety of methods of making compressed tablets. See, e.g., Remington: The Science and Practice of Pharmacy, Nineteenth Edition, Gennaro Ed. (1995) Vol. II pp. 1615–1649; Niwa et al. (1994) Pharm. Res. 11:478–484; and Franz et al. (1980) J. Pharm. Sci. 69:621–628. Interestingly, little has changed since the basic tableting method described in 1843. British Patent No. 9977. A number of parameters must be taken into account in tablet formulation such as moisture content and the physical characteristics of the substituents. This makes tablet formulation somewhat empirical. See, e.g., Lipps et al. (1994) J. Pharm. Sci. 83:937–947; Drissi-Alami et al. (1993) J. Pharm. Belg. 48:43–52; Ishino et al. (1990) Chem. Pharm. Bull. (Tokyo) 38:1987–1992; Sendall et al. (1986) J. Pharm. Pharmacol. 38:489–493; Fetzer et al. (1986) J. Pharm. Pharmacol. 38:254–258; Reading et al. (1984) J. Pharm. Pharmacol. 36:421–426; Paronen et al. (1983) J. Pharm. Pharmacol. 35:627–635; Nakagawa et al. (1982) Chem. Pharm. Bull. (Tokyo) 30:1401–1407; Elsabbagh et al. (1981) Pharmazie 36:488–492; Naito et al. (1977) J. Pharm. Sci. 66:254–259; Healey et al (1974) J. Pharm. Pharmacol. 26 Suppl: 41P–46P; and York et al. (1972) J. Pharm. Pharmacol. 24 Suppl:47P–56P.

A number of diluents are used in tableting to increase the bulk of the tablet to a practical size for compression. Diluents commonly used for this purpose include dicalcium phosphate dihydrate, tricalcium phosphate, calcium sulfate, lactose, spray-dried lactose, pregelatinized starch, microcrystalline cellulose, cellulose, kaolin, mannitol, sodium chloride, dry starch and powdered sugar. Certain diluents, particularly mannitol, lactose, sorbitol, sucrose and inositol, are used to make chewable tablets. Sucrose and mannitol are most frequently used in chewable tablets (AmStar and ICI Americas, respectively). Microcrystalline cellulose (Avicell, FMC) is a nonfibrous form of cellulose obtained by spray-drying washed, acid-treated cellulose and is available in several grades that range in average particle size from 20–100 $\mu$m. Certain drawbacks are inherent in the use of any diluent and they must be chosen based on their intended use and reactivity with the drug. For instance, the combination of amine bases or amine salts with lactose in the presence of an alkaline lubricant, results in losses in the bioavailaibility of the active agent and tablets that discolor on aging.

The superior tableting properties of lactose have, however, resulted in its widespread use and intensive study as a tableting excipient. Sebhatu et al. (1994) Pharm. Res. 11:1233–1238; Vromans et al. (1985) Acta Pharm. Suec. 22:163–172; Vromans et al. (1985) Pharm Weekbl [Sci] 7:186–193; De Boer et al. (1986) Pharm Weekbl [Sci] 8:145–150; Van Kamp et al. (1986) Acta Pharm. Suec. 23:217–230; Vromans et al. (1986) Acta Pharm. Suec. 23:231–241; Georgakopoulos et al. (1983) 38:240–243; and York et al. (1973) J. Pharm. Pharmacol. 25:Suppl:1P–11P. Hydrous lactose does not flow and its use is limited to tablet formulations prepared by the wet granulation method. Both anhydrous lactose and spray-dried lactose have good flowability and compressibility and can be used in direct compression provided a suitable disintegrant and lubricant are present in the tablet. Other constraints to the use of lactose in tableting are discussed below.

Agents used to impart cohesive qualities to the powdered material are referred to as binders or granulators. They impart a cohesiveness to the tablet formulation which insures the tablet remaining intact after compression, as well as improving the free-flowing qualities by the formulation of granules of desired hardness and size.

The selection of a particular formulation of components for use in tableting is determined by a variety of parameters including the physical characteristics of the finished tablet. The exact formulation will contain a number of components, each chosen to impart a specific function and together to effect the specific properties desired in a tablet and is largely determined empirically. The physical characteristics of tablets are measured in terms of strength, friability uniformity of dimensions and disintegration time. Tablet strength, also termed hardness or tensile strength, is a measure of the cohesiveness of a tablet. Hardness is defined as the resistance of the tablet to chipping, abrasion or breakage under conditions of storage, transportation and handling. There are a number of machines manufactured for measuring hardness, such as the Hebelein, distributed by Vector. If a tablet is too hard, it may not disintegrate in the required period of time or meet the dissolution specification; if it is too soft, it will not withstand handling during subsequent processing, packaging, etc. Friability, is the ability of a tablet to resist abrasion. Friability is measured by tumbling tablets and determining the weight loss. Tumbling can be performed manually or mechanically, for instance by a Roche friabilator. The thickness, weight, disintegration time and content uniformity of a tablet must be relatively invariant from run to run. Tablets may be subject to further processing such as coating prior to packaging. A wide variety of coatings are known in the art.

Trehalose, ($\alpha$-D-glucopyranosyl-$\alpha$-D-glucopyranoside), is a naturally occurring, non-reducing disaccharide which was initially found to be associated with the prevention of desiccation damage in certain plants and animals which can dry out without damage and can revive when rehydrated. Trehalose is available commercially in the dihydrate form, having a 8–10% water content. Trehalose has been shown to be useful in preventing denaturation of proteins, viruses and foodstuffs during desiccation. See U.S. Pat. Nos. 4,891,319; 5,149,653; 5,026,566; Blakeley et al. (1990) Lancet 336:854–855; Roser (July 1991) Trends in Food Sci. and Tech. 166–169; Colaco et al. (1992) Biotechnol. Internat. 345–350; Roser (1991) BioPharm. 4:47–53; Colaco et al. (1992) Bio/Tech. 10:1007–1011; and Roser et al. (May 1993) New Scientist, pp. 25–28. Trehalose dihydrate is available in good manufacturing process (GMP) grade crystalline formulations. A method of making a desiccant, anhydrous form of trehalose is described in EP patent publication no. 600 730. This method involves heating a trehalose syrup in the presence of a seed crystal and recovering the anhydrous trehalose.

Trehalose is found extensively in such diverse animal and plant species as bacteria, yeast, fungi, insects and invertebrates. In many insects, it is the major blood sugar. The only major source for man is dietary in foods such as mushrooms and yeast products. Madsarovova-Nohejlova (1973) Gastroenterol. 65:130–133.

Trehalose is described for use in a peritoneal dialysis system in U.S. Pat. No. 4,879,280 where it is mentioned as one of several disaccharides as a replacement for the prior art system which utilized glucose. Trehalose is mentioned for use in the dialysis system as a disaccharide that will not be readily cleaved to glucose and thus avoid raising the blood glucose level. Trehalose has also been described as suitable for use in parenteral formulations primarily because it can be sterilized by autoclaving without the browning associated with conventional parenteral formulations. Japanese Patent No. 6-70718.

Trehalose is a common component of the human diet and information is available on its metabolism. Following oral ingestion, trehalose is not absorbed intact through the gastrointestinal tract, as only monosaccharides can pass throughout the intestinal epithelium. Ravich and Bayless (1983) Clin. Gast. 12:335–356. Trehalose is metabolized by the enzyme trehalase into two molecules of glucose. Sacktor (1968) Proc. Natl. Acad. Sci. USA 60:1007–1014. Trehalase is a normal constituent of most mammalian bodies, including humans, and has been identified in human serum, lymphocytes and the liver, but is principally located in the brush border of the intestinal tract and the renal proximal tubules. Belfiore et al. (1973) Clin. Chem. 19:447–452; Eze (1989) Biochem. Genet. 27:487–495; Yoshida et al. (1993) Clin. Chim. Acta 215:123–124; and Kramers and Catovsky (1978) Brit. J. Haematol. 38:4453–461. Trehalase is a membrane bound protein of the human and animal intestinal tract. Bergoz et al. (1981) Digestion 22:108–112; Riby and Galand (1985) Comp. Biochem. Physiol. 82B:821–827; and Chen et al. (1987) Biochem. J. 247:715–724.

The process by which intestinal trehalase metabolizes exogenous trehalose has been described. Intestinal hydrolases, such as trehalase, are surface components attached to the external side of the luminal membrane microvilli, and may be anchored to the membrane by phosphatidylinositol. Maestracci (1976) Biochim. et Biophys. Acta 433:469–481; and Galand (1989) Comp. Biochem. Physiol. 94B:1–11. Trehalose is hydrolyzed on the brush border surface of the enterocyte, where the two glucose molecules produced are released in close proximity to the membrane. Ravich and Bayless (1983). Glucose molecules are absorbed at the membrane by an active rather than a passive transport system. This physiological function was originally described in conjunction with other sugars as "membrane contact digestion."

U.S. Pat. Nos. 4,678,812 and 4,762,857 describe methods and compositions of tableting powders using the S-1 process of powder formation. These patents describe a process of forming an aqueous mixture of all the components of the finished tablet including trehalose, active ingredients, excipients, etc., spraying the aqueous mixture onto the surface of a moving bath of perfluorocarbon liquid, followed by lyophilization of the frozen droplets to dried powders. The S-1 method is used to prevent the formation of amorphous forms of trehalose. Also, the mixing of all the components in aqueous solution prior to formation of the powder an integral part of the claimed invention as it is required to achieve the necessary degree of homogeneity, that is, batch to batch standardization. The S-1 method is described more fully in U.S. Pat. Nos. 3,932,943 and 3,721,725. Trehalose is also described for use as a desiccant in food products, cosmetics and pharmaceuticals. EP publication nos. 606 753 A2; and 636 693.

All references cited herein, both supra and infra, are hereby incorporated herein by reference.

DISCLOSURE OF THE INVENTION

It has now been found that trehalose, in a variety of physical forms, can be used to produce tablets of even higher quality than lactose tablets without use of the S-1 process or the necessity of combining all the components in aqueous solution prior to powder formation. Additionally, trehalose does not undergo chemical reactions, typical of the Maillard reaction, with amino, amine or amido groups as seen with the reducing sugar lactose. Further, it has also been found that the amorphous forms of trehalose are preferred in tableting and produce tablets of very high quality and homogeneity. The invention also includes methods of making various forms of anhydrous trehalose.

The invention encompasses methods of producing tablets from various physical forms of powdered trehalose and combinations thereof. The forms of trehalose include, trehalose dihydrate (TD), which is in crystalline form, amorphous trehalose (AT), which is in vitreous form, and the anhydrous forms of trehalose, anhydrous amorphous trehalose (AAT) and anhydrous crystalline trehalose (ACT). The anhydrous trehalose powders (AAT and ACT) may contain AAT, and/or ACT. As used herein, "trehalose" refers to any physical form of trehalose including anhydrous, partially hydrated, fully hydrated and mixtures and solutions thereof.

As used herein, anhydrous trehalose refers to any physical form of trehalose containing less than about 2 percent water. The anhydrous forms of trehalose may contain from about 0–2% water and still retain superior properties in tableting. Amorphous trehalose (AT) contains about 2–9% water and TD contains about 9–10% water. The invention encompasses tablets formed with or without a disintegrant. The tablets including disintegrants have been found to dissolve rapidly and completely to form an aqueous solution of the active agent.

In one method of making tablets, an active agent is incorporated into a solution of trehalose and dried to form a trehalose matrix. The trehalose matrix obtained will initially be in the form of AT. This matrix is then blended with trehalose and any other excipients and tableted.

Provided the active agent is heat stable in the presence of trehalose, the AT can be further treated to obtain AAT, ACT or mixtures thereof prior to use in tableting. The tablets thus obtained are also encompassed by the invention.

The invention also encompasses methods of making tablets by mixing at least one physical form of trehalose in powder form; an effective amount of an active agent; excipients, if any; and forming tablets from the mixture. The tablets thus obtained are also encompassed by the invention.

The invention also encompasses tablets composed of AAT and/or ACT with or without TD and/or AT optionally including other tableting excipients. Different formulations of these components result in tablets with a wide variety of properties suitable for use with a number of varying types of active agents.

The invention also encompasses methods of making anhydrous trehalose from TD. The method of making AAT includes heating crystalline TD or AT at a temperature, for a duration of time, under reduced pressure (vacuum) and under conditions sufficient to remove the water molecules. The method of making ACT comprises heating crystalline TD at a temperature and under conditions sufficient to yield ACT. By varying the temperature and pressure applied during drying, mixtures of different ratios of AAT and ACT can be obtained. Thus, a desired mixture of the two forms can be made by regulating the initial treatment conditions rather than treating the batches separately and then weighing and mixing. This decreases the steps required and lowers batch to batch variability.

BRIEF DESCRIPTION OF THE DRAWINGS

In FIG. 1, the melting point is 215° C.

In FIG. 2, the melting point is 101.5° C.

In FIG. 3, the glass transition temperature (Tg) is 117° C.

In FIG. 4 the Tg is 105° C.

In FIG. 5, the Tg is 100° C.

In FIG. 6, the Tg is 69° C.

In FIG. 7, the Tg is 84° C.

In FIG. 8, the glass transition temperature, Tg, is 42° C.

In FIG. 9, the melting point is 100° C.

MODES FOR CARRYING OUT THE INVENTION

In addition to the active agent, tablets may contain a variety of other components or "excipients." Diluents, typically powders, add bulk to make the tablet a practical size for compression. In compressed tablet formation, the dry components are mixed thoroughly, treated to produce a more homogeneous mixture and then compressed into tablets. For instance, in producing Phenobarbital tablets, dried Phenobarbital sodium, lactose, starch, talc and magnesium stearate (65, 26, 20, 20 and 0.3 mg each, respectively, per tablet) are thoroughly mixed. The mixture is then compressed into slugs. The slugs are ground and screened to 14 to 16-mesh granules. The granules are then recompressed into the final tablet. Although energy consumptive, these steps are necessary to assure the most homogeneous distribution possible.

Lactose is the most frequently studied tableting excipient, particularly spray dried lactose. Spray dried lactose contains about 15% anhydrous lactose. Pure amorphous lactose does not produce tablets as it lacks the plasticity imparted by the crystalline lactose. Thus, amorphous lactose must be mixed with crystalline lactose in order to produce tablets. The greater the concentration of amorphous lactose, the longer the dissolution time. This is because amorphous lactose does not disintegrate but, rather, dissolves from the surface. Increasing amounts of amorphous lactose also impart unacceptable hardness to tablets. Further, lactose reacts with amino groups via the Maillard reaction. Thus, lactose is unsuitable for use where the active agent or any excipients contain labile amino groups. With the increased use of peptides and peptide mimetics, for instance in oral tolerization regimens, lactose would be unsuitable as an excipient.

It has now been found that the use of trehalose produces tablets of superior qualities by all parameters tested. Unlike amorphous lactose, tablets made from AT do not suffer from excess hardness and readily dissolve under the appropriate conditions. In addition, trehalose, as a non-reducing sugar, does not react with amino groups, and its surprising resistance to hydrolysis to yield reducing sugars enables its use where the active agent or any excipients contain labile amino groups. Importantly, as demonstrated in the examples presented herein, in addition to producing tablets of superior physical properties, trehalose, and particularly AAT, provide increased stability of the active agent incorporated into the tablet and anhydrous trehalose further provides protection of the active agent from ambient humidity. Although TD also forms tablets, it can decrease the stability of moisture-sensitive and hygroscopic active agents; however, inclusion of anhydrous trehalose in the tablets can alleviate this problem. Without being bound by any one theory, applicants believe that the protection from humidity offered by anhydrous trehalose is due to its absorption of water molecules to produce TD and that this sequestration of the atmospheric water molecules from the active agents decreases the exposure of the active agent to moisture.

The use of anhydrous trehalose as a diluent in tablets imparts improved physical properties compared to prior art diluents. For instance, the active agents are more stable, in the case of AAT, the tablets are more resistant to humidity. In the following examples, anhydrous trehalose shows clear superiority over TD in maintaining the stability of an active agent.

Although singular forms may be used herein, more than one active agent and more than one excipient may be present in the compositions described and claimed herein. Determination of the types and effective amounts of these components is within the skill of one in the art.

Once the powders for tableting are formed as described herein, they are formulated into tablets by any method known in the art. Suitable methods include, but are not limited to, milling, fluid bed granulation, dry granulation, direct compression, spheronization, spray congealing and spray-dying. Detailed descriptions of tableting methods are provided, for instance in Remington: The Science and Practice of Pharmacy, 19th ed. Vol. 11 (1995) Mack Publishing Co., Pennsylvania. Preferably, the tablets are formed by compression.

The present invention encompasses methods of making tablets by combining the tableting components in solution or suspension in an aqueous solvent processing this to form a substantially homogeneous powder and forming tablets from the powder. Excipients, if any, can be added either to the aqueous solvent and processed to form a powder or added to the powder. The amount of active agent and trehalose added to the solvent, are ones which assure an effective amount in each tablet formed. The amount of trehalose should be one which assures commercially acceptable standards of hardness, friability and dissolution time. The effective amount of active agent is one which assures at least one unit dose per tablet formed. Typical effective amounts of active agent are described for instance in the Physician's Desk Reference.

The processing of the dissolved or suspended components to form a powder is not by the S-1 process. The S-1 process was used to avoid producing any form of amorphous trehalose. Applicants have now found that not only is the S-1 process unnecessary, time-consuming and labor intensive, but that the amorphous forms of trehalose positively contribute to tablets made from trehalose.

Any method other than the S-I process known in the art of forming trehalose powders can be used in the methods described herein. Preferably, the processing methods described below are used but other methods are suitable.

By forming a substantially homogeneous mixture, it is meant that the mixture forms tablets that meet the commercial standards in terms of uniformity of composition. That is, there is a lack of variability between tablets within a lot and between lots to assure conformance with commercial standards.

As described below, the processing step can be such that the powdered trehalose is in the form of TD, AT, AAT, ACT or mixtures thereof (one or more of these forms).

The tablets may also be formed by combining effective amounts of trehalose, active agent and excipients if any, in the powder form, processing the powder to form a substantially homogeneous mixture and forming tablets from the mixture. The trehalose can be TD, AT, AAT, ACT or mixtures thereof. The trehalose can initially be TD and can then be processed as described below to obtain the other physical forms.

The invention further encompasses methods of making tablets containing both ACT and AAT and the compositions obtained thereby. The two anhydrous forms of trehalose may be mixed in a wide variety of ratios to obtain tablets of varying properties. TD and/or AT may also be incorporated to impart desired characteristics of hardness, friability and dissolution times. The anhydrous trehalose mixtures can be obtained according to the methods described herein or by any other method known in the art. The components, anhydrous trehalose, TD, active agent, other binders and excipients, if any, are combined, mixed, and formulated into tablets by any method known in the art. Alternatively, the active agent can be mixed in solution with trehalose, dried and then subjected to a combination of heat and vacuum which yields a mixture of ACT and AAT. The proper combination of heat and vacuum can be determined empirically and depends on the amount and type of active agent and the ratio of AAT to ACT desired. Applying heat without vacuum results in purely ACT whereas heat and the upper ranges of vacuum results in just AAT. By varying the amount of vacuum applied, the ACT:AAT ratio can be controlled. The ratio of the various physical forms can be determined for instance by DSC. Practically speaking, the optimal mixture of anhydrous trehalose forms will be determined empirically by determining which processing conditions yield tablets with the most desirable characteristics.

The invention further encompasses tablets composed of TD and/or anhydrous trehalose and varying amounts of AT. As used herein, AT is non-crystalline or "vitreous" trehalose containing water in an amount greater than 2% (anhydrous)

but less than 10% (fully hydrated). AT imparts stability on active agents dried therein and thus dry solid trehalose formulations containing active agents can readily be tableted with any other form of trehalose as a totally compatible tableting excipient. If the AT formulation produced is dried sufficiently to yield at least a mixture of anhydrous trehalose and AT, the dry solid formulation containing the active agent can be used directly in tableting without the use of additional anhydrous trehalose as a tableting excipient. Although this would be more energy consuming, it would yield the advantage of a homogeneously distributed active agent at a molecular level within the tablet which may be desirable under certain circumstances.

Preferably, the AT formulation is produced by first making a foamed trehalose glass (FTG) containing the active agent and making a powder of the FTG. The AT formulation may also be produced by freeze-drying or spray drying. In both cases the active agent and TD can be mixed in solution and then used to produce the dry powder formulation. This incorporates the active agent directly in the tablet without the need for subsequent processing prior to tableting to combine the dry active agent and binder. The various components can, of course, be combined in the dry form and mixed by any method known in the art such as milling, granulating, blending and grinding. This is the most common method of forming powders for tableting and is suitable for use where homogeneity at a molecular level is not required.

FTG is made from a solution of trehalose containing the active agent in any suitable buffer formulation which is then subject to a drying protocol to yield a dry expanded AT foamed matrix containing the active agent. Briefly, the solution is subject to a primary drying step to produce a syrup and then a secondary drying step to "boil" off the remaining solvent. In the primary drying step, the solvent is evaporated to obtain a syrup. Typically, a "syrup" is defined as a solution with a viscosity in the region of $10^6$–$10^7$ Pascal seconds. The viscosity of the syrup is preferably such that when the syrup boils, evaporation from the increased surface area, provided by extensive bubble formation, results in its vitrification. The syrup is not defined as a fixed concentration, but rather by the viscosity resulting from evaporating the bulk of the solvent from the mixture. This initial drying step can be performed under pressure less than ambient. The syrup obtained from the primary drying step is exposed to a reduced pressure to effect boiling of the syrup. As used herein, "boiling" is defined as the point at which the vapor pressure of the mixture is equal to or exceeds the external pressure to which the sample is exposed. The boiling step results in formation of bubbles which greatly increases the evaporative surface area of the syrup. This allows increased evaporation of residual solvent and the FTG vitrifies as a solid foam of the bubbles which result from the boiling step. The endpoint of the boiling step can be determined by an increase in sample temperature, which is preferably maintained for a time period sufficient to ensure thorough drying. This varies from sample to sample but is easily determinable by one of skill in the art. Subsequent to the final drying step, the FTG is powdered and used with either AAT or ACT to make tablets containing the active agent in a continuous trehalose matrix.

The invention encompasses novel methods of producing anhydrous trehalose from TD. The methods produce AAT, ACT and mixtures thereof. The anhydrous trehalose obtained is particularly suitable for use as a tableting excipient. Although any methods known in the art may be used to make the anhydrous trehalose, both crystalline and amorphous, used in tableting, the novel methods presented herein are preferred. These methods reproducibly produce high quality anhydrous trehalose powders, simply, economically and without the use of solvents. The methods are fast, simple and do not require the complicated, expensive and time-consuming methods of the prior art. In fact, unlike all known prior art methods, no solvents need to be used. For instance, spray drying can be avoided and freeze drying with its variable results and high energy consumption can be avoided.

Figure 1:
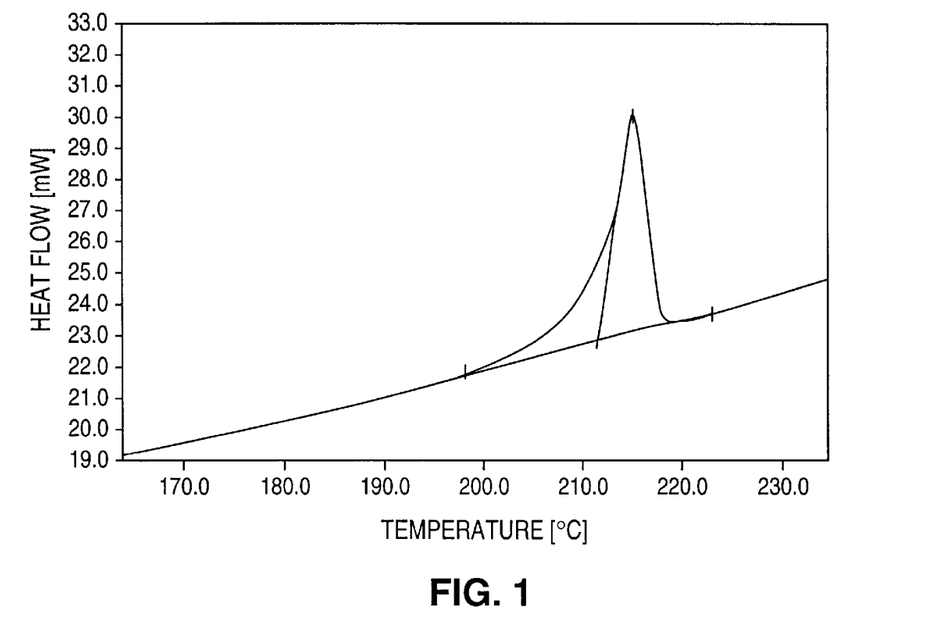
FIG. 1 is a graph depicting the differential scanning calorimetry (DSC) trace of the crystalline form of anhydrous trehalose formed by the removal of water from the crystalline dihydrate (TD). In each of the figures depicting DSC traces, the temperature was raised in increments of 10.0° C./min. The profile shows a characteristic crystalline melt endotherm.

The method of making ACT includes the steps of heating TD, obtained from any source, at a temperature, for a duration of time and under conditions sufficient to remove the water molecules. The heating is preferably performed under ambient, atmospheric, pressure. Preferably, the heating is at about 50–105° C. More preferably, the heating is at about 60–90° C. Most preferably, the heating is at about 70° C. Typically, the preferred heating duration is about 4–96 hours. More preferably, the heating duration is about 12–72 hours. Most preferably, the heating duration of time is about 24 hours. Typically, the TD is heated at 70° C. for 12–24 hours to produce ACT. It has now been shown that the method described herein produces ACT. As shown in FIG. 1, and described more fully in Example 1a, the DSC analysis of the product obtained by heating TD for 48 hours at 70° C., shows a sharp endothermic peak at about 200° C. indicative of the melting of the crystalline form of the anhydrous trehalose powder. For comparison of the ACT to the crystalline TD form, compare FIG. 2, which depicts the DSC analysis of crystalline TD, and FIG. 1. The DSC trace of FIG. 2 also shows the sharp endothermic peak characteristic for the melting of the crystalline form, but at the much lower temperature of about 96° C., the specific melting point of crystalline TD.

Figure 3:
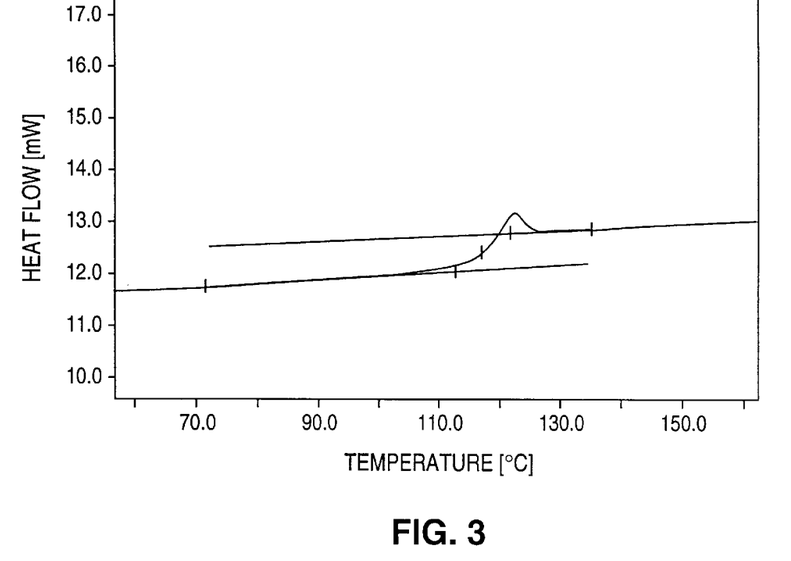
FIG. 3 is a graph depicting the DSC trace of AAT formed by the removal of water from TD under vacuum.
Figure 4:
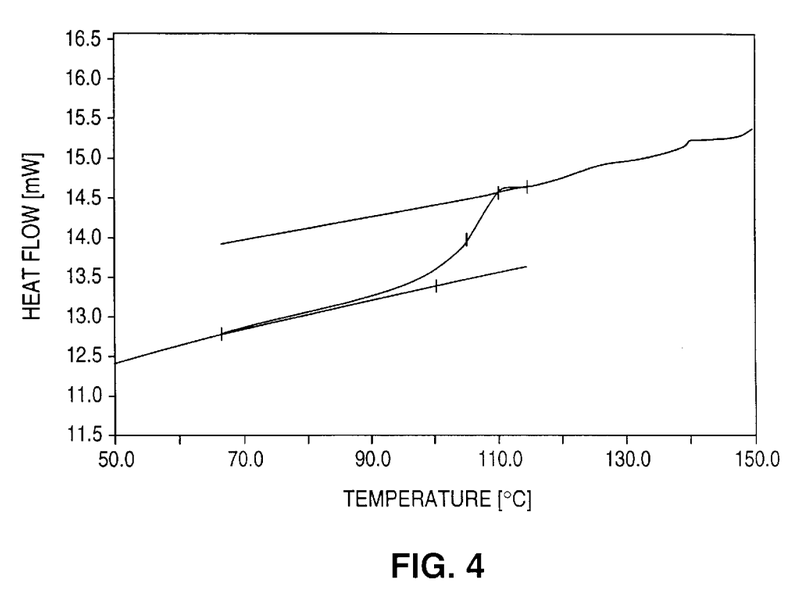
FIG. 4 is a graph depicting the DSC trace of AAT formed by quenching from the melt.
Figure 5:
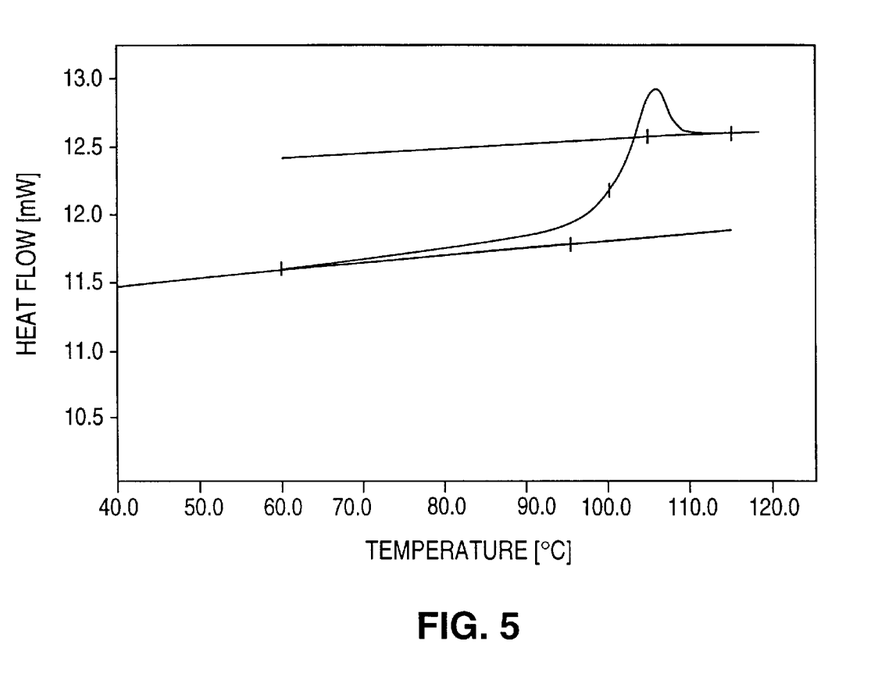
FIG. 5 is a graph depicting the DSC trace of AT formed by freeze-drying from solution.
Figure 6:
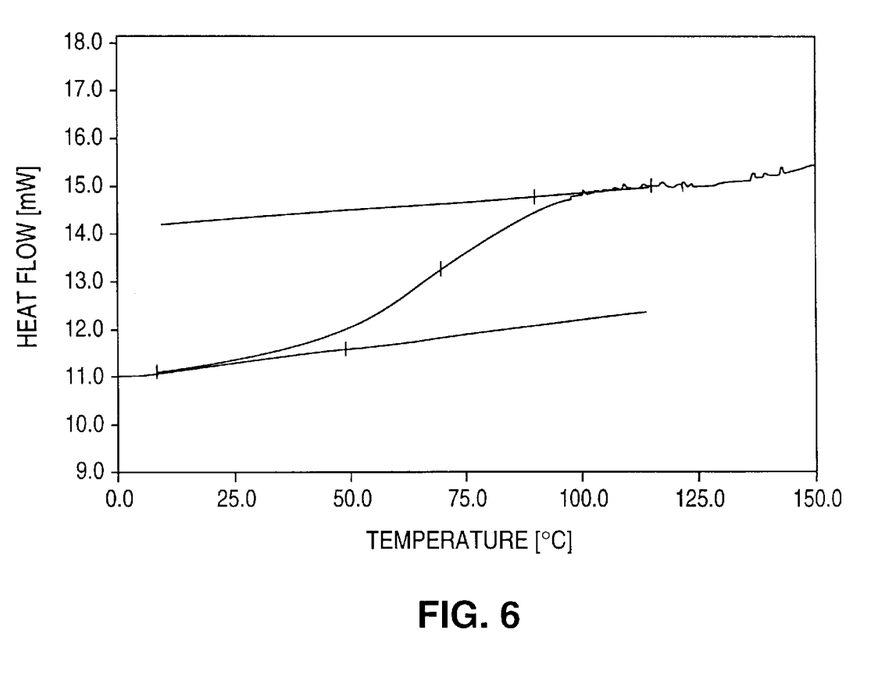
FIG. 6 is a graph depicting the DSC trace of AT formed by spray-drying from solution.

Applying reduced pressure during the heating of TD results in the formation of AAT. Typically, the preferred reduced pressure is about 1–30,000 mTorr. More preferably, the reduced pressure is about 10–10,000 mTorr. Most preferably, the reduced pressure of is about 750 mTorr. Typically, the sample is heated under reduced pressure for 18–24 hours. FIG. 3 shows the DSC analysis of AAT obtained by heating crystalline TD at 70° C. for 24 hours and at 1.5 Torr. This is described more fully in Example 1b. Note that the trace obtained does not have the single distinct endothermic peak characteristic of crystalline trehalose, but shows the glass transition typical of amorphous matrices. FIGS. 4–6 show the DSC traces of AT produced by FTGs, spray drying and freeze drying of trehalose solutions containing active agents. The glass transition temperatures (Tg) seen are dependent on the residual water contents of the AT matrix with increased water contents corresponding to lower measured Tgs. These are described more fully in Examples 1c–1f.

Any tableting aids, or excipients, known in the art can be included in the formulations. Excipients other than diluents include, but are not limited to, binders, lubricants, disintegrants, coloring agents and flavoring agents.

Binders, or granulators, impart cohesive qualities to the powdered material. Materials commonly used as binders include starch, gelatin and sugars such as sucrose, glucose, dextrose, molasses and lactose. Natural and synthetic gums that are also used include acacia, sodium, alginate, extracts of Irish moss, panwar gum, ghatti gum, mucilage of isapol husks, carboxymethylcellulose etc. Any other suitable binders known in the art may be added including, but not limited to, Ludipress, Kollidon, polyvinyl pyrolidone (PVP) and HES. Kollidon is sold as Kollidon VA64 (BASF) and is a polyvinyl pyrolidone based binder. Ludipress (BASF) is a commercial tableting mixture of lactose and PVP. Byco A (Croda) is degraded gelatin of 2500–4000 M. Wt. range. HES (NPBI) is hydroxyethyl starch. As discussed below, under certain conditions, the addition of binders is necessary to achieve the correct degree of hardness in the RS tablets.

Lubricants are used for a number of purposes, including preventing adhesion of the blended materials to the surface of the die and punch, reducing interparticle friction, facilitating the ejection of the tablets from the die cavity and improving the flow of the tablet granulation.

In the examples presented herein, magnesium stearate was routinely used as a lubricant, and is the preferred lubricant. Any other suitable lubricant known in the art may be used including, but not limited to, talc, calcium stearate, stearic acid, hydrogenated vegetable oil, lutrol and polyethylene glycol (PEG). Disintegrants are added to facilitate breakup or disintegration of the tablet before or after administration. Coloring agents make the dosage form more esthetic in appearance and may serve as identification. Flavoring agents are usually added to provide sweetness to chewable or dissolvable tablets. The invention encompasses tablets formed from trehalose with or without any excipient or any suitable combinations of excipients.

The active agent can be any known in the tableting art and is typically a pharmaceutical agent, biological modifier, or diagnostic component. Pharmaceutical agents include, but are not limited to, antipyretic and antiinflammatory drugs, analgesics, antiarthritic drugs, antispasmodics, antidepressants, antipsychotics, tranquilizers, antianxiety drugs, narcotic antagonists, antiparkinsonism agents, cholinergic agonists, chemotherapeutic drugs, immunosuppressive agents, antiviral agents, antibiotic agents, parasiticides, appetite suppressants, antiemetics, anticholinergics, antihistaminics, antimigraine agents, coronary, cerebral or peripheral vasodilators, hormonal agents, contraceptives, antithrombotic agents, diuretics, antihypertensive agents, cardiovascular drugs, opioids and vitamins. Detailed parameters and discussions of such active agents can be found, for instance, in the Physician's Desk Reference (1995) 49th ed., Medical Economics Data Production Co. New Jersey. An amount of active agent is used such that there is an "effective amount" in each tablet formed. An effective amount is thus a single unit dosage which may vary depending on whether the tablets are obtained over the counter or via prescription. For instance, Sudafed® brand nasal decongestant contains 30 mg pseudoephedrine hydrochloride per tablet when obtained over the counter and 60 mg per tablet when obtained via prescription.

The chemical structures of such active agents, include, but are not limited to, lipids, organics, proteins, synthetic peptides, natural peptides, peptide mimetics, peptide hormones, steroid hormones, D amino acid polymers, L amino acid polymers, oligosaccharides, polysaccharides, nucleotides, oligonucleotides, nucleic acids, protein-nucleic acid hybrids, antigens and small molecules. Suitable proteins include, but are not limited to, enzymes, biopharmaceuticals, growth hormones, growth factors, insulin, monoclonal antibodies, interferons, interleukins, collagen and cytokines. Suitable organics include, but are not limited to, vitamins, neurotransmitters, antimicrobials, antihistamines, analgesics and immunosuppressants. Suitable steroid hormones include, but are not limited to, corticosteroids, estrogen, progesterone, testosterone and physiologically active analogs thereof. Suitable nucleic acids include, but are not limited to, DNA, RNA and physiologically active analogs thereof.

Active agents commonly used in diagnostics include, but are not limited to, dyes, antibodies, enzymes, hormones and antibiotics.

Any other tableting methods or formulations known in the art can also be used. For instance, the invention encompasses coated tablets, chewable tablets, effervescent tablets, molded tablets or tablet triturates, encapsulated tablets, microencapsulated tablets and sustained release tablets. The tablets produced are suitable for use in any animal including humans. Although the tablets described herein are for human use, suitable veterinary formulations are readily fashioned given the skill of one in the art and the Examples and Description presented herein.

The following examples are provided to illustrate, but not limit, the claimed invention. Powders used in tableting must have excellent flow properties and consistent particle size. For the purposes of these trials, particle size was not stringently controlled, but powders were formulated to have flow characteristics suitable for tablet production. The flow characteristics obtained were found to enable loading the tablet die without difficulty. A sieving procedure can be incorporated to ensure a more even particle size. This is essential in larger batches to guarantee thorough mixing of the components and it is well within the skill of one in the art to devise a suitable sieving procedure.

EXAMPLE 1

Methods of Making AAT and ACT.

1a. Formation of ACT

Figure 2:
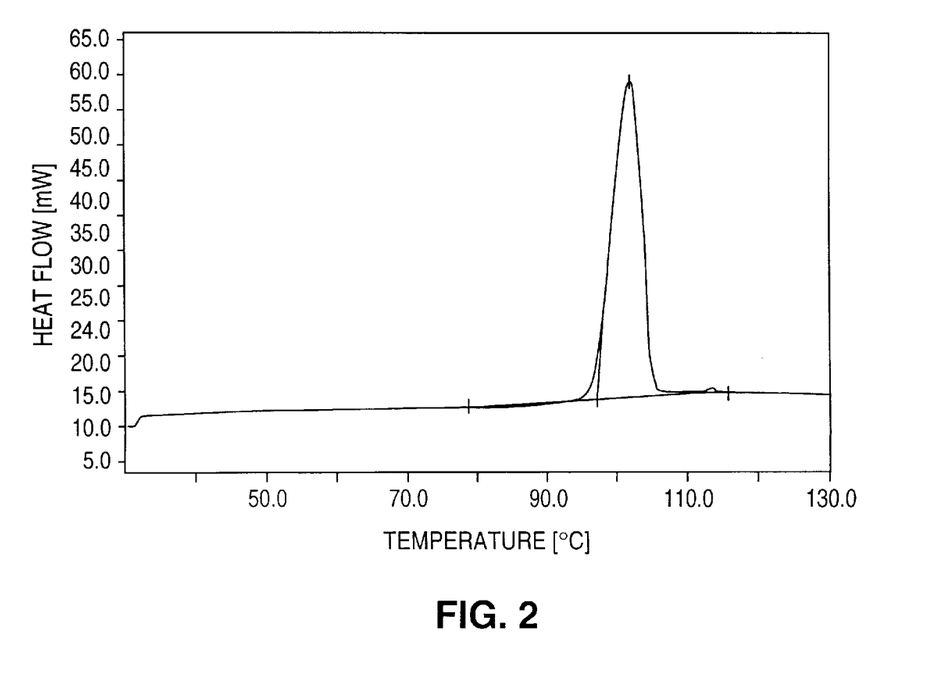
FIG. 2 is a graph depicting the DSC trace of TD, the profile obtained is indicative of crystalline TD with the characteristic melt endotherm at a lower temperature.

Crystalline TD was incubated in open trays at temperatures of 55° C., 70° C. and 80° C. in a standard laboratory oven for 24–72 hours. Samples were assayed for water content by Karl Fischer analysis and selected samples were also analyzed by DSC. Surprisingly, the samples all showed water contents ranging from 0.1–2%, even those heated at just 55° C. FIG. 1 shows the DSC trace of a sample heated at 70° C. for 48 hours. The water content of the sample was 0.33%. The sample showed a crystalline melt at approximately 210–216° C. characteristic of the melting temperature of ACT. This endotherm is distinct from the melt endotherm at the lower temperature of 96–101° C. characteristic of TD seen in the DSC analysis of crystalline dihydrate as shown in FIG. 2.

1b. Formation of AAT

Crystalline TD was incubated in open trays for 16–24 hours in either a Heraus vacuum oven with a reduced pressure of 1.5 Torr, or in a FTS freeze drier with a reduced pressure of 30 mTorr, and the shelf temperature set at 60° C. Samples were again assayed for water content by Karl Fischer analysis and selected samples were also analyzed by DSC. Samples typically showed water contents lower than those in Example 1a, ranging from 0.1–1.5%. FIG. 3 shows the DSC trace of a sample heated at 60° C. for 24 hours in a vacuum oven at 1.5 Torr. The water content of the sample was below 0.1%. Surprisingly, the sample no longer showed a crystalline melt at approximately 215° C., but instead showed a glass transition of 116–117° C. characteristic of the amorphous form of trehalose demonstrating the formation of AAT.

1c. Formation of AAT by Quenching from the Melt

Crystalline TD was heated at 96–100° C. with a minimum quantity of water to produce an isotropic melt which was transferred to an oven at 185° C. for a few minutes before cooling the melt to produce a clear trehalose glass. The glass was then ground in a Waring blender to give a fine powder. Samples were again assayed for water content by Karl Fischer analysis and selected samples were also analyzed by DSC. Samples typically showed water contents ranging from 0.1–2%. FIG. 4 shows the DSC trace of a typical sample having a glass transition of 100–102° C. characteristic of the amorphous form of trehalose again demonstrating the formation of AAT.

1d. Formation of AAT Containing Active Agent by Freeze Drying

Samples containing a solution of 20% (w/v) trehalose were frozen at 5° C./hr to −40° C. and dried under vacuum of 30 mTorr at a shelf temperature of −35° C. for 40 hrs, followed by a further 2 hrs drying at the raised shelf temperature of 25° C. in an FTS freeze-drier. A dry powder typical of freeze drying was obtained. Samples typically showed water contents ranging from 0.1–2%. FIG. 5 shows the DSC trace of a typical sample with water content of 0.79%, showing a glass transition of 100–101° C. characteristic of the amorphous form of trehalose again demonstrating the formation of AAT.

1e. Formation of AAT Containing Active Agent by Spray Drying

Samples containing a solution of 20% (w/v) trehalose were spray dried in a lab-scale Buchi spray drier at a range of inlet temperature of 150–180° C. at a flow rate of 10% of the pump capacity. Samples typically showed water contents higher than in Examples 1a–d ranging from 0.5–5%. FIG. 6 shows the DSC trace of a typical sample with water content of 4.5%, showing a glass transition of 65–70° C. characteristic of the amorphous form of trehalose. Thus this method produces AAT suitable for incorporation into tablets in combination with anhydrous trehalose and TD.

1f. Formation of AAT Containing an Active Agent in FTG

Figure 7:
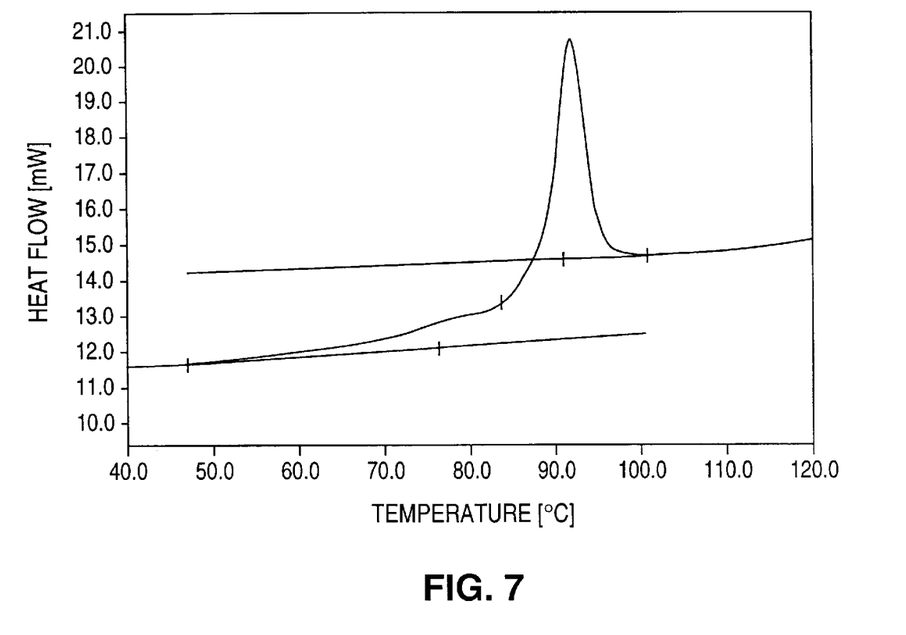
FIG. 7 is a graph depicting the DSC trace of AT formed by vacuum-drying from solution to produce a foamed trehalose glass (FTG).
Figure 8:
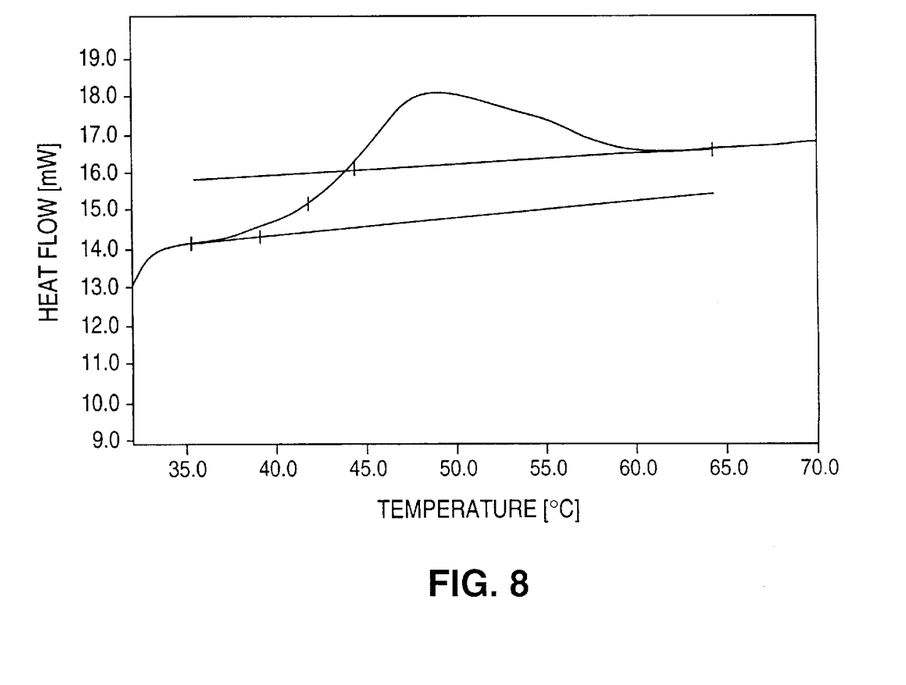
FIG. 8 is a graph depicting the DSC trace of AT containing active peptide in a FTG.

300 μl aliquots of a solution of 43.4 mg/ml trehalose containing 66 mg/ml of an antimicrobial peptide was dried in 10 ml polypropylene tubes (10 mm diameter) in the FTS drier. Samples, at 25° C., were loaded onto a shelf in the drier that had been preheated to 35° C. The vacuum pressure in the chamber was progressively reduced to 20 Torr over 10 minutes. This pressure was held for a further 30 minutes before the pressure was further reduced to 30 mTorr. After 17 hours, the shelf temperature was increased to 50° C. This shelf temperature was maintained for 3 hours after which the cycle was stopped. The FTGs produced have an open plug-like structure similar to freeze-dried materials. Moisture content was typically 1.1 to 2 % (w/w). FIG. 7 shows the DSC trace of a typical sample with water content of 1.59% showing a glass transition of 83–84° C. characteristic of the amorphous form of trehalose.

EXAMPLE 2

Use of AAT and ACT in Tablet Production

The following example utilizes the amorphous and crystalline forms of anhydrous trehalose, for the laboratory scale production of tablets. The anhydrous trehalose was manufactured by heating crystalline TD at 60° C., at atmospheric pressures to obtain ACT or under vacuum with heat to obtain the AAT as described in Examples 1a and 1b, respectively.

The blends used in the tableting of anhydrous trehalose contained either single forms of anhydrous trehalose or mixtures thereof, and also optionally contained a number of commercially used binders such as Kollidon VA64, Ludipress, BycoA and HES and lubricants such as magnesium stearate, sodium lauryl sulfate and Lutrol.

The production of rapidly dissolving tablets was again achieved by the addition of a volatile salt to the tableting blend followed by the removal of the salt under vacuum to obtain a porous tablet that showed increased dissolution rates compared to tablets of the same blends without the volatile salt incorporated. Aliquots of 0.5 g of powder were weighed out into a 0.5 inch Manesty type die. The tablet was formed by hammering onto the upper punch (A single light positioning blow, followed by a stronger single blow). The tablets were of a convex oval shape and at least 3 mm thick. On release from the die, the tablets were stored in sealed vials. In tablets formed from blends containing ammonium bicarbonate, the volatile salt was removed under a vacuum of 1.5 Torr at 60° C. for six hours to yield porous, rapidly dissolving tablets which were again stored in sealed vials prior to analysis. Disintegration and dissolution of the tablets was studied in distilled water at 28° C. with gentle agitation.

The results obtained on tableting the various blends of anhydrous trehalose and disintegration and dissolution are presented in Tables 1 and 2 respectively. In Table 1, * stands for anhydrous trehalose, K stands for Kollidon and B stands for BycoA. Table 2 shows the effect of increased porosity on rate of disintegration/dissolution of selected tablets. Similar results were obtained for the formation of tablets from these formulations using the automated Manesty F3 tableting press.

TABLE 1

| | Composition (Wt %) | | | | |
|---|---|---|---|---|---|
| Sample | Trehalose form | Tab. aid | Amm. bicarb. | Mg stearate | Comments |
| 1 | 99.5 ACT | — | — | 0.5 | Good |
| 2 | 64.97 ACT | HES 4.8 | 29.6 | 0.53 | Excellent |
| 5 | 99.5 AAT | — | — | 0.5 | Good |
| 6 | 69.5 AAT | — | 30 | 0.5 | Good |
| 7 | 59.5* | — | 40 | 0.5 | Some lamination |
| 8 | 49.5* | — | 50 | 0.5 | Occasional lamination |
| 14 | 39.5* | B 10 | 50 | 0.5 | Mostly good |
| 15 | 44.5%* | B 5 | 50 | 0.5 | Good. Few laminate after storage |
| 18 | 69.5* | — | 30 | 0.5 | Excellent |
| 19 | 67.5* | B 2 | 30 | 0.5 | Good |
| 22 | 50* | — | 50 | — | Excellent |
| 25 | 55* | K 5 | 40 | — | Excellent |
| 27 | 54.5* | K 5 | 40 | 0.5 | Excellent |

TABLE 2

| Sample | Disint | Dissol | Comments |
|---|---|---|---|
| 1 | 22 secs | 2.5 mins | — |
| 2 | — | 7.5 mins | no disintegration |
| 14 | — | 1 min | — |
| 15 | 15 secs | 45 secs | most dissolves in 30 secs |
| 18 | — | 4 mins | no disintegration |
| 19 | — | 2 mins | no disintegration |
| 22 | 10 secs | 45 secs | — |
| 25 | 15 secs | 1 min | — |
| 27 | 10 secs | 1 min | — |

The results presented in Table 2 indicate that removal of volatile salt to give porous tablets significantly increased the disintegration and dissolution rates of the tablets produced. Complete removal of the volatile salt by was assessed by difference in tablet weight before and after vacuum treatment. AT compresses better than the FTG and volatile salt can be incorporated in up to at least 50 weight %. This leads to a highly porous matrix after the volatile salt has been removed. AT alone remains a good binder, though some loss in intrinsic strength is seen in tablets of blends incorporating ammonium bicarbonate and especially once the volatile salt has been removed. Without a binder of some kind, these porous tablets are very fragile and a balance is therefore essential between a high proportion of volatile and inclusion of a small percentage of binder. These porous tablets dissolve rapidly when compared to tablets formed from trehalose alone; the time for full dissolution is generally reduced from 10–15 minutes down to less than 1 minute.

EXAMPLE 3

Use of AAT for Making Tablets Containing Active Agent: Stability Enhancement Over Use of Crystalline TD Pre-formulated powders, containing AAT and a synthetic vasoactive peptide, together with binders and lubricants such as Kollidon VA64 (BASF), Citric acid (BDH), Aerosil 200 (Degussa), Magnesium stearate (BDH), Sodium lauryl sulfate (BDH), Polyethylene glycol 8000 (BDH), Glyceryl monostearate (Akzo Nobel) and Lutrol F68 (BASF) were blended using a Braun coffee grinder for a few seconds, before being sieved through a 30 mesh (500 micron) screen. Tableting was performed on a Manesty F3 single station, direct compression press. The speed was set at about 60–70 tablets per minute and compression was approximately 1–1.5 tons. The flow of the blend was controlled to give the desired weight distribution of the tablets produced.

The general appearance of the tablets was recorded. Hardness was measured on a Schleuniger-4M hardness tester. Friability of the tablets was estimated by vigorously shaking a number of tablets together and visually inspecting for fragmentation. Dissolution was tested using 5 tablets, suspended in aluminum baskets, in 1l of stirred (500 rpm speed) deionised, distilled water at 37° C. The dissolution time recorded, was that when all the soluble excipients had disappeared from view. Hygroscopicity of the tablets was assayed by weight change after 24 hours incubation at several relative humidities. Stability of the vasoactive peptide was assayed by HPLC analysis. Tables 3–5 illustrate selected formulations that were tableted and tested as above. Table 3 shows the compositions of active agent incorporated in the FTG tableted with AAT as the tableting excipient. Table 4 shows the incorporation of active agent directly into the AAT tablet by simply mixing the active agent with AAT to yield the tableting blend. Table 5 shows the effect of conversion of AAT to dihydrate on tableting of blend.

TABLE 3

| No. | % | Mg/ tablet | Raw Material | Tot. Qty (gms) |
|---|---|---|---|---|
| 1 | 95.42 | | AAT + 10% FTG containing active peptide at 1.11 mg/g | 171.76 19.08 |
| 2 | 0.16 | | Citric acid | 0.32 |
| 3 | 4.0 | | Kollidon VA64 | 8.0 |
| 4 | 0.02 | | Aerosil 200 | 0.04 |
| 5 | 0.4 | | Magnesium stearate | 0.8 |
| Total | 100 | 50 | | 200 |

The results presented in Table 3 indicate that excellent tablets were formed. The tablets had good binding properties and little excess dust was produced. The dosing of the die was very reproducible and therefore consistent weight was achieved.

TABLE 4

| No. | % | Mg/ tablet | Raw Material | Tot. Qty (gms) |
|---|---|---|---|---|
| 1 | 95.4 | | AAT | 190.80 |
| 2 | 0.0185 | | Vasoactive peptide | 0.0370 |
| 3 | 0.16 | | Citric acid | 0.32 |
| 4 | 4.0 | | Kollidon VA64 | 8.0 |
| 5 | 0.02 | | Aerosil 200 | 0.04 |
| 6 | 0.4 | | Magnesium stearate | 0.8 |
| Total | 100 | 50 | | 200 |

The results presented in Table 4 indicate that excellent tablets were formed. The dosing was again consistent. Good binding properties were observed with the use of Kollidon.

TABLE 5

| No. | % | Mg/ tablet | Raw Material | Tot. Qty (gms) |
|---|---|---|---|---|
| 1 | 93.0 | | AAT + 10% FTG (blank preparation) | 167.40 18.60 |
| 2 | 2.0 | | Lutrol F68 | 4.0 |
| 3 | 4.48 | | Kollidon VA64 | 8.96 |
| 4 | 0.02 | | Aerosil 200 | 0.04 |
| 5 | 0.5 | | Magnesium stearate | 1.0 |
| Total | 100 | 50 | | 200 |

Figure 9:
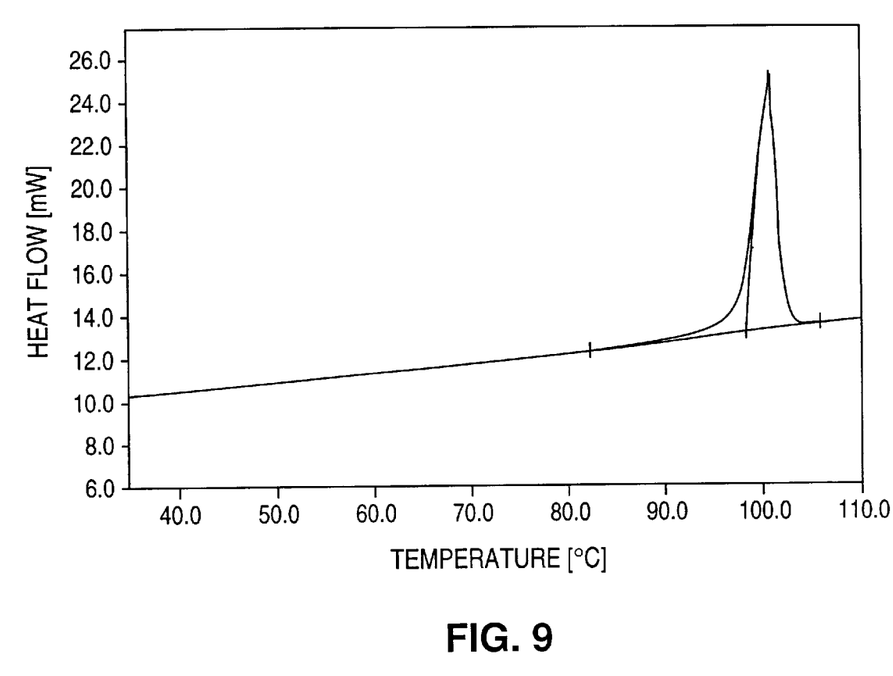
FIG. 9 is a graph depicting the DSC trace of the FTG containing active peptide (sample as in FIG. 8) after storage at ambient humidity depicting the melting of dihydrate formed due to devitrification on exposure to the atmosphere.

The results presented in Table 5 indicate that excellent tablets were formed when the above blend was used and hard tablets were produced with a high sheen. However, after exposure of the blend to ambient humidities for 48 hours, the tablets formed showed marked lamination. Exposure of the blend to ambient humidity resulted in the conversion of the AAT to the crystalline dihydrate as demonstrated by the DSC analysis shown in FIG. 9.

Without exception, excellent tablets were produced with AAT. A mixture of lubricants was found to be most effective in the formulation and a binder generally gave tablets with a higher sheen. Dissolution times were all within the specified 5 minutes. Table 6 shows the measures of physical hardness and dissolution times of the tablets formed using the blends in Tables 3–5.

TABLE 6

| Batch Ref. | Hardness (KP) | Average Weight (mg) | Dissolution time (mins) |
|---|---|---|---|
| Blend in Table 1 | 1.0–1.2 | 50 | 1.75–2 |
| " | 1.4 | 54 | 2 |
| Blend in Table 2 | 1.5 | 52 | 2.75 |
| " | 1.5–1.7 | 50 | 2.5 |
| Blend in Table 3 | 2.2–2.3 | 51 | 2.25 |
| " | 1.2–1.4 | 50 | 2 |

Table 7 shows data for moisture absorption by AAT tablets after 24 hours and 96 hours exposed to specific relative humidities. The selective adsorption of the water taken up by the anhydrous trehalose results in the partitioning of water by the tableting excipient thus protecting the active at the different RHs.

TABLE 7

| Conditions | Weight % change | | Appearance |
| --- | --- | --- | --- |
| | 24 hours | 96 hours | |
| Atmos. 45% R.H. | +8.24 | No | no change |
| 75% R.H. | +8.60 | further | no change |
| Atmos 45% R.H. | +8.10 | change | no change |
| 75% R.H. | +8.40 | observed | no change |

The weight % change was measured based on the original weight of ten tablets. The results indicate that the tablets adsorb moisture to around 8–9% by weight with a devitrification of the AAT to give crystalline dihydrate tablets. Table 8 shows the dissolution of trehalose tablets when exposed to 45% R.H. for 96 hours. Table 9 shows the enhanced stability of active agent in tablets using AT over crystalline TD as a tableting excipient. Though the latter show more rapid disintegration and dissolution rates (Table 8), the stability of the active agent may be compromised as shown by the loss in activity observed on storage (Table 9).

TABLE 8

| No. | Run No. | Exposed to 45% R.H. | Dissolution time |
| --- | --- | --- | --- |
| 1 | 2 | yes | <30 seconds immediate disintegration |
| 2 | 2 | no | 2 minutes no disintegration |
| 3 | 3 | yes | <30 seconds immediate disintegration |
| 4 | 3 | no | 2.25 minutes no disintegration |

TABLE 9

| FORMULATION | INITIAL | 1 WEEK 70° C. | 2 WEEKS 70° C. |
| --- | --- | --- | --- |
| AAT | 100 | 97 | 89 |
| AAT | 100 | 89 | 88 |
| TD | 100 | 42 | 43 |

In conclusion, AT (in various blends) was successfully tableted using a commercial single stage press. The tablets produced had hardnesses between 1 and 2.3 KP and friabilities <1% and no capping or lamination was seen. The tablets all dissolved within 3 minutes. The tablets containing active agent formed using anhydrous trehalose as a tableting excipient showed enhanced stability of the active agent compared to tablets formed using the crystalline dihydrate. This may be particularly important for the tableting of labile active agents.

EXAMPLE 4

Tableting a Labile Antibiotic

The antibiotic potassium clavulanate is particularly labile as it is prone to chemical degradation on exposure to moisture. This chemical degradation is readily apparent in tablets containing the antibiotic as it results in browning of the tablets. In order to determine whether AAT offered increased protection from chemical degradation compared to TD, the following experiment was performed.

11.8 g of AAT or TD were blended in a mortar and pestle with 1 g of potassium clavulanate and tableted as described in Example 1. The resulting tablets were then stored at ambient temperature and humidity. Within 16 hours, browning was observed in the TD tablets but not in the AAT tablets. If the tablets were stored at 80° C. and ambient humidity, the browning was observed in 2 hours in the TD tablets. Even after the 8 hours, however, no browning was observed in the AAT tablets.

Although the foregoing invention has been described in some detail by way of illustration and example for purposes of clarity and understanding, it will be apparent to those skilled in the art that certain changes and modifications may be practice. Therefore, the description and examples should not be construed as limiting the scope of the invention which is delineated by the appended claims.

We claim:

1. A method of making tablets comprising the steps of:
   (a) combining components comprising an amount of anhydrous trehalose sufficient to act as an effective diluent in the tablets formed and an amount of an active agent such that each tablet formed contains an effective amount of active agent and an amount of aqueous solvent sufficient to suspend or dissolve the anhydrous trehalose and active agent;
   (b) processing the product of step (a) to form a powder comprising a substantially homogeneous mixture of the components, wherein the powder is formed using a process other than spray freeze drying; and
   (c) forming tablets from the powder.

2. The method according to claim 1, wherein the components of step a) further comprise at least one excipient.

3. The method according to claim 1, further comprising the steps of b1) adding excipients to the powder; and b2) mixing the excipients and powder to form a substantially homogeneous mixture.

4. The method according to claim 1 or 2, wherein the excipient is selected from the group consisting of diluents, binders, lubricants, disintegrants, coloring agents and flavoring agents.

5. The method according to claim 4, wherein the diluent is selected from the group consisting of trehalose, dicalcium phosphate, dihydrate, calcium, tricalcium phosphate, sulfate, lactose, spray-dried lactose, pregelatinized starch, microcrystalline cellulose, cellulose, kaolin, mannitol, sodium chloride, dry starch and powdered sugar.

6. The method according to claim 4, wherein the binder is selected from the group consisting of starch, gelatin, sugars, natural and synthetic gums, Ludipress, Kollidon, polyvinyl pyrrolidone and hydroxyethyl starch.

7. The method according to claim 3, wherein the lubricant is selected from the group consisting of talc, calcium stearate, stearic acid, hydrogenated vegetable oil, lutrol, polyethylene glycol and magnesium stearate.

8. The method according to claim 1, wherein the processing in step (b) produces powdered trehalose in a form selected from the group consisting of trehalose dihydrate, amorphous trehalose, anhydrous amorphous trehalose, anhydrous crystalline trehalose or mixtures thereof.

9. The method according to claim 1, wherein the tablets are formed by compression.

10. The method according to claim 1, further comprising the step of: d) coating the tablets.

11. A method of making tablets comprising the steps of:
   (a) combining, in substantially dry form, components comprising an amount of anhydrous trehalose sufficient to act as an effective diluent in the tablets formed and an amount of an active agent such that each tablet formed contains an effective amount of active agent;

(b) processing the product of step (a) to form a substantially homogeneous mixture; and (c) forming tablets from the powder of step (b).

12. The method according to claim 11, wherein the components of step a) further comprise at least one excipient.

13. The method according to claim 12, wherein the excipient is selected from the group consisting of diluents, binders, lubricants, disintegrants, coloring agents and flavoring agents.

14. The method according to claim 13, wherein the diluent is selected from the group consisting of trehalose, dicalcium phosphate, dihydrate, calcium, tricalcium phosphate, sulfate, lactose, spray-dried lactose, pregelatinized starch, microcrystalline cellulose, cellulose, kaolin, mannitol, sodium chloride, dry starch and powdered sugar.

15. The method according to claim 13, wherein the binder is selected from the group consisting of starch, gelatin, sugars, natural and synthetic gums, Ludipress, Kollidon, polyvinyl pyrrolidone and hydroxyethyl starch.

16. The method according to claim 13, wherein the lubricant is selected from the group consisting of talc, calcium stearate, stearic acid, hydrogenated vegetable oil, lutrol, polyethylene glycol and magnesium stearate.

17. The method according to claim 11, wherein the anhydrous trehalose is trehalose dihydrate, amorphous trehalose, anhydrous amorphous trehalose, anhydrous crystalline trehalose and mixtures thereof.

18. The method according to claim 11, wherein the tablets are formed by compression.

19. The method according to claim 11, further comprising the steps of: d) coating the tablets.

20. The method according to claim 1 or 11, wherein the active agent is selected from the group consisting of antipyretic and anti-inflammatory drugs, analgesics, antiarthritic drugs, antispasmodics, antidepressants, antipsychotics, tranquilizers, antianxiety drugs, narcotic antagonists, antiparkinsonism agents, cholinergic agonists, chemotherapeutic drugs, immuno-suppressive agents, antiviral agents, antibiotic agents, parasiticides, appetite suppressants, antiemetics, anticholinergics, antihistaminics, antimigraine agents, coronary vasodilators, cerebral vasodilators, peripheral vasodilators, hormonal agents, contraceptives, antithrombotic agents, diuretics, antihypertensive agents, cardiovascular drugs, opioids, and vitamins.

21. A composition comprising a tablet produced by the method of claim 1, 2, 11 or 12.

22. A method of producing anhydrous trehalose comprising the steps of heating trehalose dihydrate at a temperature, for a duration of time and under conditions sufficient to reduce the water content to about 0 to 2%.

23. The method according to claim 22, wherein the anhydrous trehalose is anhydrous crystalline trehalose.

24. The method according to claim 22, wherein the heating occurs at reduced pressure under conditions sufficient to yield amorphous anhydrous trehalose.

25. The method according to claim 24, wherein the reduced pressure is from 1–30,000 mTorr.

26. The method according to claim 22 or 24, wherein the temperature for heating trehalose dihydrate is from about 50–105° C.

27. The method according to claim 26, wherein the temperature for heating trehalose dihydrate is from about 60–90° C.

28. The method according to claim 27, wherein the temperature for heating trehalose dihydrate is at about 70° C.

29. The method according to claim 22 or 24, wherein the duration of time is about 4–36 hours.

30. The method according to claim 29, wherein the duration of time is from about 12–72 hours.

31. The method according to claim 30, wherein the duration of time is from about 48 hours.

* * * * *